United States Patent
Sano et al.

(10) Patent No.: US 7,153,270 B2
(45) Date of Patent: Dec. 26, 2006

(54) DEVICE FOR SECURING LIVING BODY BY PRESSING

(75) Inventors: Yoshihiko Sano, Kyoto (JP); Minoru Taniguchi, Uji (JP); Takahide Tanaka, Otsu (JP); Takefumi Nakanishi, Nagaokakyo (JP); Tomonori Inoue, Kyoto (JP); Hiroya Nakanishi, Kyoto (JP); Yukiya Sawanoi, Nara (JP)

(73) Assignee: Omron Healthcare Co., Ltd., Kyoto (JP)

( * ) Notice: Subject to any disclaimer, the term of this patent is extended or adjusted under 35 U.S.C. 154(b) by 75 days.

(21) Appl. No.: 11/054,959

(22) Filed: Feb. 11, 2005

(65) Prior Publication Data

US 2005/0182332 A1 Aug. 18, 2005

(30) Foreign Application Priority Data

Feb. 18, 2004 (JP) ............................. 2004-041735

(51) Int. Cl.
*A61B 5/02* (2006.01)

(52) U.S. Cl. ............... 600/499; 600/490; 600/492; 600/494; 600/485

(58) Field of Classification Search ........ 600/490–503, 600/485; 606/201–203; 602/13, 27, 20–23
See application file for complete search history.

(56) References Cited

U.S. PATENT DOCUMENTS

| 4,667,672 | A  | * | 5/1987  | Romanowski       | 606/202 |
|-----------|----|---|---------|------------------|---------|
| 5,454,831 | A  | * | 10/1995 | McEwen           | 606/202 |
| 5,511,551 | A  | * | 4/1996  | Sano et al.      | 600/499 |
| 6,186,967 | B1 |   | 2/2001  | Messina          |         |
| 6,478,745 | B1 | * | 11/2002 | Nakagawa et al.  | 600/499 |
| 6,656,141 | B1 |   | 12/2003 | Reid             |         |
| 6,913,575 | B1 | * | 7/2005  | Nishibayashi et al. | 600/490 |
| 6,916,289 | B1 | * | 7/2005  | Schnall          | 600/500 |
| 2002/0099299 | A1 |   | 7/2002 | Inagaki          |         |
| 2002/0173735 | A1 |   | 11/2002 | Lewis            |         |
| 2005/0182331 | A1 | * | 8/2005 | Millay et al.    | 600/499 |

FOREIGN PATENT DOCUMENTS

| EP | 1224907 A | 7/2002 |
| JP | 55-56605  | 4/1980 |
| JP | 59-97645  | 6/1984 |

(Continued)

OTHER PUBLICATIONS

European Search Report dated Oct. 7, 2005, directed to corresponding EP Application No. 05002180.7.

(Continued)

*Primary Examiner*—Robert L. Nasser
*Assistant Examiner*—Navin Natnithithadha
(74) *Attorney, Agent, or Firm*—Morrison & Foerster LLP

(57) ABSTRACT

A device for securing a living body by pressing includes a living body pressing air bag, a curled elastic member of an approximately cylindrical shape, disposed on the outside of the living body pressing air bag and changeable in size in a radial direction, and a curled elastic member pressing air bag, disposed on the outside of the curled elastic member and inflated to press an outer peripheral surface of the curled elastic member inward to reduce a diameter of the curled elastic member, to thereby press the living body pressing air bag against the living body via the curled elastic member. This can provide a living body pressing and securing device provided with a novel automatic cuff winding mechanism that can simplify and downsize the winding mechanism, hardly causes skin tension on the body surface, and ensures uniform winding strength over the entire surface of the pressed site.

9 Claims, 12 Drawing Sheets

FOREIGN PATENT DOCUMENTS

| | | |
|---|---|---|
| JP | 2-135003 | 11/1990 |
| JP | 4-338450 | 11/1992 |
| JP | 06-038931 | 2/1994 |
| JP | 08-154905 A | 6/1996 |
| JP | 10-314123 | 12/1998 |
| JP | 2000-060808 | 2/2000 |
| JP | 2002-209858 | 7/2002 |
| JP | 2004-254882 | 9/2004 |

OTHER PUBLICATIONS

Japanese Office Action mailed Mar. 14, 2006, directed to counterpart JP Application No. 2004-041735.

* cited by examiner

DEVICE FOR SECURING LIVING BODY BY PRESSING

BACKGROUND OF TH INVENTION

1. Field of the Invention

The present invention relates to a device for securing a living body by pressing (hereinafter, also referred to as a "living body pressing and securing device"), and more particularly, to a living body pressing and securing device for measuring a blood pressure that can automatically wind a cuff for use in a blood pressure monitor or the like to a living body to secure the living body by pressing.

2. Description of the Background Art

To measure a blood pressure value, generally, a cuff provided with a living body pressing fluid bag for pressing an artery located within the living body is wound around the body surface, and arterial pressure pulse waves caused in the artery by inflation/deflation of the living body pressing fluid bag are detected to measure the blood pressure value. Here, the cuff refers to a band-shaped structure having a bladder, which can be wound around a portion of a living body, for use in measurement of arterial pressure of an upper limb, a lower limb or the like by introducing fluid such as gas or liquid into the bladder. Thus, the cuff represents the concept including the living body pressing fluid bag as well as means for winding the living body pressing fluid bag around the living body.

In a conventional blood pressure monitor, the cuff was wound around the living body by a subject or the like, so that there occurred variation in the cuff winding strength, which caused variation in the blood pressure values measured. Thus, in recent years, blood pressure monitors provided with an automatic cuff winding device have become widespread, which enables automatic winding of the cuff around the living body. With the blood pressure monitor provided with the automatic cuff winding device, constant winding strength is reproduced for each time of measurement, which ensures stable and accurate measurement and also eliminates the burdensome, cuff winding job.

An automatic cuff winding device mounted to a blood pressure monitor normally employs a configuration where an elastic member of an approximately cylindrical shape is arranged on the outside of a living body pressing fluid bag for pressing the living body. This elastic member is for binding and securing the living body pressing fluid bag from around the periphery, and for pressing the living body pressing fluid bag against the living body upon measurement of a blood pressure value. With the function of this elastic member, pressure loss of the living body pressing fluid bag upon measurement is reduced, and accurate measurement of the blood pressure value is ensured.

For the above-described automatic cuff winding device, a variety of mechanisms have been proposed. For example, Japanese Patent Laying-Open No. 2000-060808 discloses an automatic cuff winding device provided with a mechanism for winding a cuff around a living body by pulling an end of the cuff formed in an approximately cylindrical shape in a tangent direction. Hereinafter, this automatic cuff winding device will be described in more detail.

FIG. 16 is a front view showing a configuration of the automatic cuff winding device disclosed in the above publication. In the automatic cuff winding device shown in FIG. 16, a cuff 115 having a living body pressing air bag and a curled elastic member contained therein is wound in an approximately cylindrical shape, and attached to a base unit 151. Cuff 115 has an end 115a in a circumferential direction secured to base unit 151, and another end 115b secured to a rotary drum 155 provided at base unit 151. Rotary drum 155 is connected to an electric motor 152 with a decelerator via a pulley 153 and a belt 154. A torque limiter is also connected to rotary drum 155, to prevent a torque greater than a predetermined level from being applied to the cuff.

With the automatic cuff winding device configured as described above, electric motor 152 with a decelerator is activated to wind cuff 115 around an upper arm that is inserted into a hollow portion formed inside the cuff 115. More specifically, electric motor 152 with a decelerator drives and rotates the rotary drum 155 to carry out winding of cuff 115, and cuff 115 reduced in diameter is wound around the upper arm. In this manner, uniform winding strength is reproduced for each time of measurement, and stable and accurate measurement is realized.

Automatic cuff winding devices provided with various mechanisms, besides the one shown in FIG. 16, have also been proposed. For example, Japanese Utility Model Laying-Open No. 02-135003 discloses a winding mechanism for winding a cuff around a living body, wherein a wire rope is wound on the outside of a cuff including a living body pressing air bag therein, an end of the wire rope is secured to a pulley that is connected to an electric motor, and the electric motor is activated to drive and rotate the pulley to pull the wire rope in a tangent direction, to reduce the diameter of the cuff to thereby wind the cuff around the living body. Further, Japanese Patent Laying-Open No. 10-314123 discloses a winding mechanism for winding a cuff around a living body, wherein a tape-shaped member is wound on the outside of a cuff having a living body pressing air bag and a curled elastic member provided therein, an end of the tape-shaped member is secured to a roller portion that is connected to an electric motor, and the electric motor is activated to drive and rotate the roller portion to pull the tape-shaped member in a tangent direction, to reduce the diameter of the cuff to thereby wind the cuff around the living body.

In each of the conventional automatic cuff winding devices described above, however, the cuff itself, having a living body pressing fluid bag and/or a curled elastic member contained therein, or the wire rope or the tape-shaped member wound on the outside of the cuff, is pulled in the tangent direction to reduce the diameter of the cuff. This causes the surface of the upper arm, which is a site subjected to measurement, is pulled by the cuff in the tangent direction, and twisted. Such twisting of the upper arm would cause skin tension on the surface of the upper arm, which becomes a source of error of measurement, hindering accurate and stable measurement of the blood pressure value.

Further, the above-described winding mechanism, which winds the cuff around the living body by pulling in the tangent direction, requires a great number of mechanical components, such as a rotary drum (roller portion) for pulling the cuff itself or a wire rope, a tape-shaped member or the like, transmission means such as a pulley, a belt, a clutch and the like, an electric motor for driving and rotating the rotary drum (roller portion), a torque limiter for preventing excessive winding, and others. This not only complicates the device configuration, but also increases the device size.

SUMMARY OF THE INVENTION

An object of the present invention is to provide a living body pressing and securing device provided with a novel automatic cuff winding mechanism that enables simplification and downsizing of the winding mechanism, hardly causes skin tension on the surface of a living body, and realizes uniform winding strength over the entire surface of the site being pressed.

The device for securing a living body by pressing according to the present invention includes: a living body pressing fluid bag for pressing a living body; an elastic member of an approximately cylindrical shape, disposed on the outside of the living body pressing fluid bag and changeable in size in a radial direction; and an elastic member pressing fluid bag, disposed on the outside of the elastic member and inflated to press an outer peripheral surface of the elastic member inward to reduce a diameter of the elastic member, to thereby press the living body pressing fluid bag against the living body via the elastic member.

In the device for securing a living body by pressing according to the present invention, the elastic member is preferably formed of segments and elastic connectors alternately arranged in a circumferential direction. In this case, each of the elastic connectors preferably connects neighboring ones of the segments and, at the same time, elastically biases the neighboring segments to keep them away from each other.

Further, in the device for securing a living body by pressing according to the present invention, the elastic member is preferably formed of a plate member wound into an approximately cylindrical shape.

Still further, in the device for securing a living body by pressing according to the present invention, it is preferable that a portion of the plate member in the vicinity of at least one end in a circumferential direction has a length in an axial direction of the plate member that is shorter than a length in the axial direction of the plate member in the vicinity of the center of the plate member in the circumferential direction.

Still further, in the device for securing a living body by pressing according to the present invention, it is preferable that an end of the living body pressing fluid bag in a circumferential direction has a tip end provided with a curved portion, and the other end of the living body pressing fluid bag in the circumferential direction has a tip end provided with a sharp portion. In this case, the curved portion is preferably configured to run on the sharp portion when the elastic member is reduced in diameter.

Still further, in the device for securing a living body by pressing according to the present invention, a low-friction member is preferably arranged between the elastic member and the living body pressing fluid bag to reduce friction therebetween.

Still further, in the device for securing a living body by pressing according to the present invention, a low-friction member is preferably arranged between the elastic member and the elastic member pressing fluid bag to reduce friction therebetween.

Still further, in the device for securing a living body by pressing according to the present invention, the low-friction member is preferably a cloth.

According to the present invention, a living body pressing and securing device having a simplified and downsized winding mechanism is realized. Further, a living body pressing and securing device provided with an automatic cuff winding mechanism that hardly causes skin tension on the body surface and ensures uniform winding strength over the entire surface of the pressed site can be realized.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, an embodiment of the present invention will be described in detail with reference to the drawings.

Figure 1:
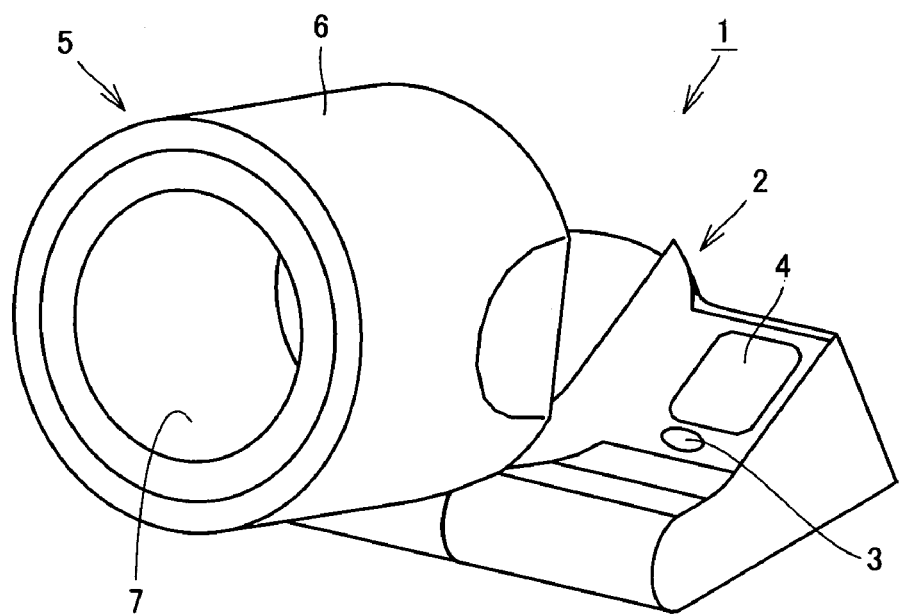
FIG. 1 is a perspective view showing an external structure of a blood pressure monitor provided with a living body pressing and securing device according to an embodiment of the present invention.

As shown in FIG. 1, a blood pressure monitor 1 incorporating a living body pressing and securing device according to an embodiment of the present invention primarily includes a base unit 2 rested on a table or the like, and a measuring portion 5 to which an upper arm as a site subjected to measurement is inserted. Provided at an upper part of base unit 2 are a control portion 3 having a power supply button for turning the power on, a measurement button for starting the measurement operation and others, and a display portion 4 for displaying a result of measurement, operation guide and others. Measuring portion 5 is attached to base unit 2 in a pivotable manner, and includes a shell 6 that is a machine frame of an approximately cylindrical shape, and a living body pressing and securing device that is housed in the inner periphery of shell 6. It is noted that the living body pressing and securing device housed in the inner periphery of shell 6 is covered with a cover 7 and not exposed in a normal use state, as shown in FIG. 1.

Figure 2:
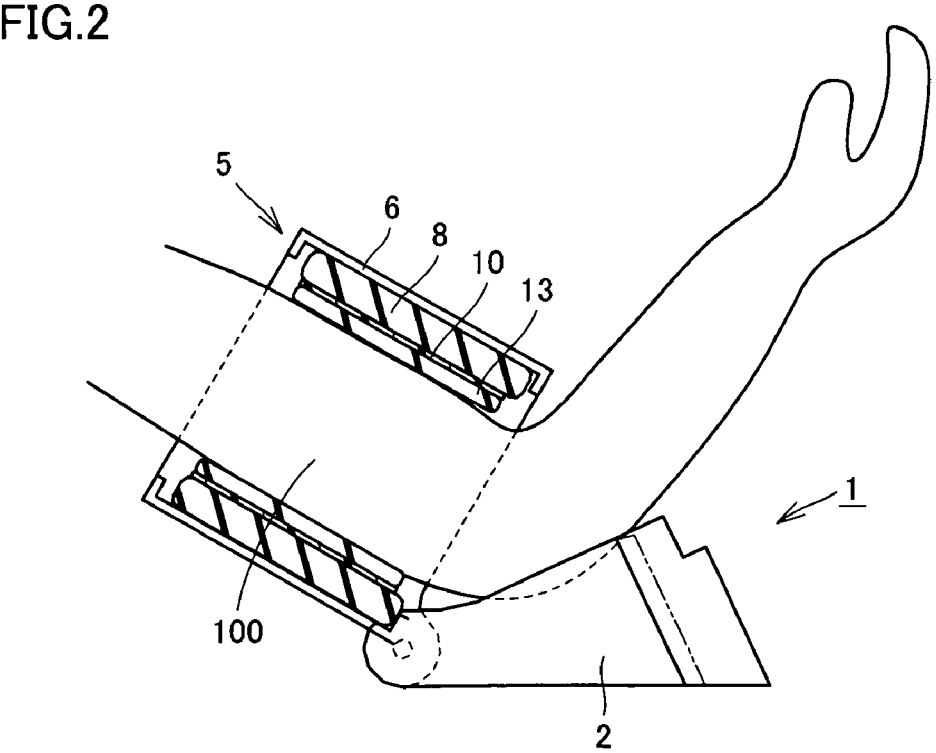
FIG. 2 is a schematic cross sectional view showing a posture when a blood pressure value is measured using the blood pressure monitor shown in FIG. 1.

Upon measurement of a blood pressure value using the above-described blood pressure monitor 1, as shown in FIG. 2, an upper arm 100 is inserted into a hollow portion located inside shell 6, and the living body pressing and securing device incorporated in the inner periphery of shell 6 presses and secures upper arm 100 to measure the blood pressure value. Blood pressure monitor 1 of the present embodiment is provided with an elbow rest at the upper part of base unit 2. Resting the elbow on this elbow rest during the measurement ensures that a posture suitable for measurement is realized without causing an unnecessary pain.

As shown in FIG. 2, the living body pressing and securing device primarily includes a living body pressing air bag 13 that is a living body pressing fluid bag for pressing a living body, a curled elastic member 10 that is an elastic member of an approximately cylindrical shape disposed on the outside of living body pressing air bag 13 and changeable in size in a radial direction, and a curled elastic member pressing air bag 8 that is an elastic member pressing fluid bag disposed on the outside of curled elastic member 10 and inflated to press the outer peripheral surface of curled elastic member 10 inward to reduce the diameter of curled elastic member 10 to thereby press living body pressing air bag 13 against the living body via curled elastic member 10. In blood pressure monitor 1 of the present embodiment, the living body pressing and securing device described above is activated to secure upper arm 100 by pressing, which is followed by inflation/deflation of living body pressing air bag 13 to detect arterial pressure pulse waves caused in the artery to thereby obtain a blood pressure value.

Figure 3:
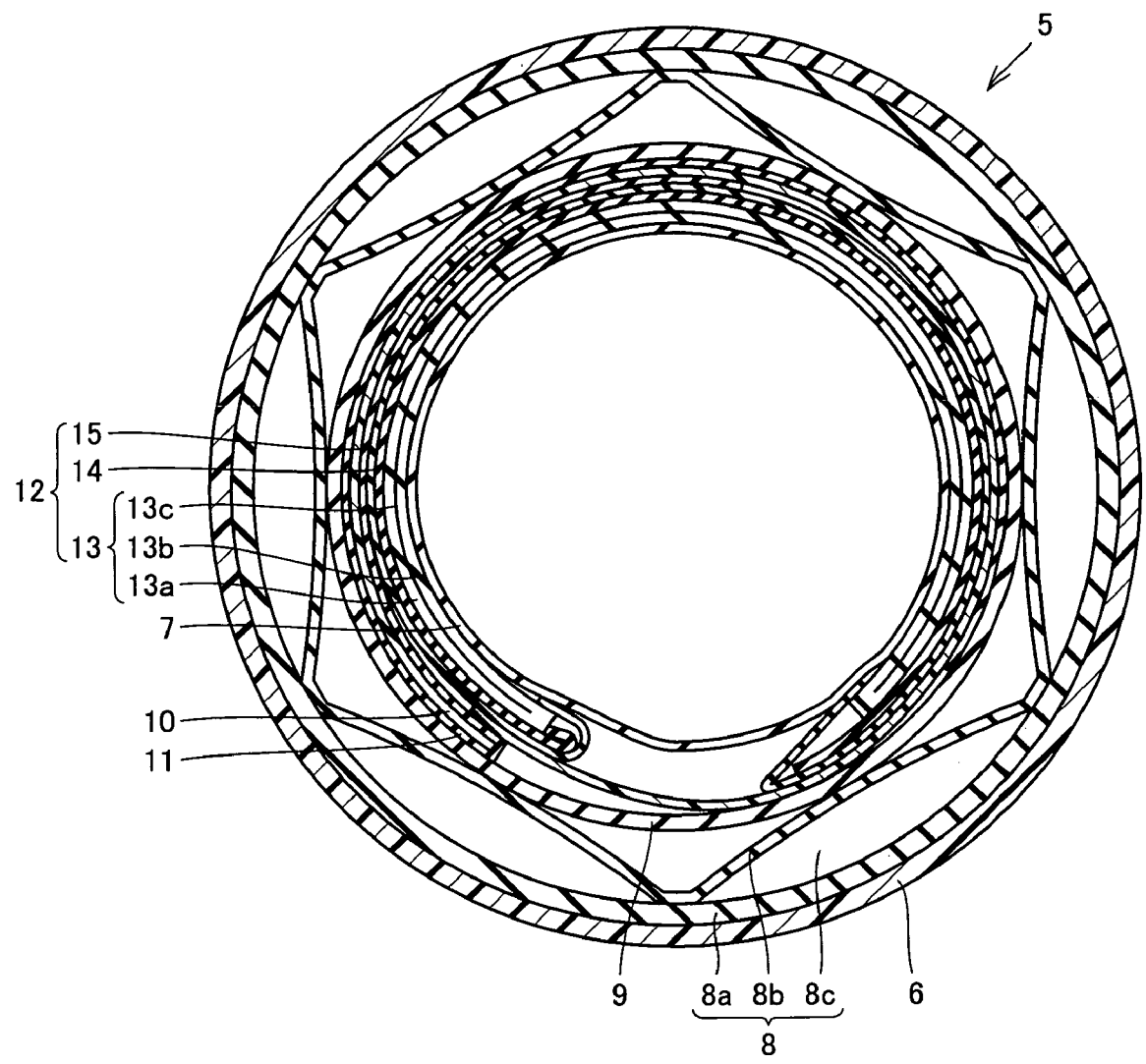
FIG. 3 is a cross sectional view showing in more detail an internal structure of a measuring portion of the blood pressure monitor shown in FIG. 1.

As shown in FIG. 3, in measuring portion 5 of blood pressure monitor 1, curled elastic member pressing air bag 8 is disposed on the inside of shell 6. Curled elastic member pressing air bag 8 includes an outer peripheral layer 8a that comes into contact with the inner peripheral surface of shell 6, and an inner peripheral layer 8b that is located on the inside of outer peripheral layer 8a. Outer peripheral layer 8a and inner peripheral layer 8b are bonded or sewn together to form a bladder 8c. Bladder 8c of curled elastic member pressing air bag 8 has its volume changeable, as it can be inflated/deflated as appropriate by means of a curled elastic member pressing air system 30 (see FIG. 4), which will be described later. In the living body pressing and securing device shown in FIG. 3, bladder 8c of curled elastic member pressing air bag 8 is partitioned into six uniform sections in the circumferential direction, which communicate with each other and can be inflated or deflated by a single air system.

Provided inside curled elastic member pressing air bag 8 all around the same is a cloth 9 that is a low-friction member for reducing sliding friction between curled elastic member 10 and curled elastic member pressing air bag 8.

Provided inside cloth 9 is curled elastic member 10 that is a plate member wound into an approximately cylindrical shape. Curled elastic member 10 is made, for example, of a resin member such as polypropylene resin, and has its ends arranged at a prescribed position in the circumferential direction. With this configuration, curled elastic member 10 undergoes elastic deformation to change in size in the radial direction when external force is applied. That is, although curled elastic member 10 is changed in size in the radial direction upon application of the external force, it recovers its original state when the external force is no longer applied. Curled elastic member 10 has its ends in the circumferential direction configured to partly overlap with each other when no external force is applied. This prevents the undesirable situation where the ends of curled elastic member 10 collide with each other and cannot move further toward the direction to reduce the diameter of curled elastic member 10.

Most part of curled elastic member 10 is covered with a cloth bag 11 that is a low-friction member formed in a bag shape. This cloth bag 11 is for reducing sliding friction between curled elastic member 10 and curled elastic member pressing air bag 8, as is the cloth 9 described above.

Provided inside curled elastic member 10 is a living body pressing unit 12 including the living body pressing air bag 13. Living body pressing unit 12 is composed of living body pressing air bag 13 that is disposed innermost, a resin plate 14 of relatively large rigidity that is a shape-keeping member disposed on the outside of living body pressing air bag 13 to keep the shape of living body pressing air bag 13 of small rigidity, and a cloth 15 that is a low-friction member disposed on the outside of resin plate 14 and in contact with the inner peripheral surface of resin plate 14.

Living body pressing air bag 13 includes an outer peripheral layer 13a that comes into contact with the inner peripheral surface of resin plate 14, and an inner peripheral layer 13b that is located on the inside of outer peripheral layer 13a and contacts the cover 7 covering the inner peripheral surface of measuring portion 5, and a bladder 13c is formed with outer peripheral layer 13a and inner peripheral layer 13b. Bladder 13c of living body pressing air bag 13 has its volume changeable, as it can be inflated/deflated as appropriate by means of a living body pressing air system 20 (see FIG. 4), which will be described later.

Resin plate 14 is a shape-keeping member for keeping the shape of living body pressing air bag 13 of relatively small rigidity to an approximately cylindrical shape. Cloth 15 is a member for reducing sliding friction between curled elastic member 10 and living body pressing air bag 13.

Figure 4:
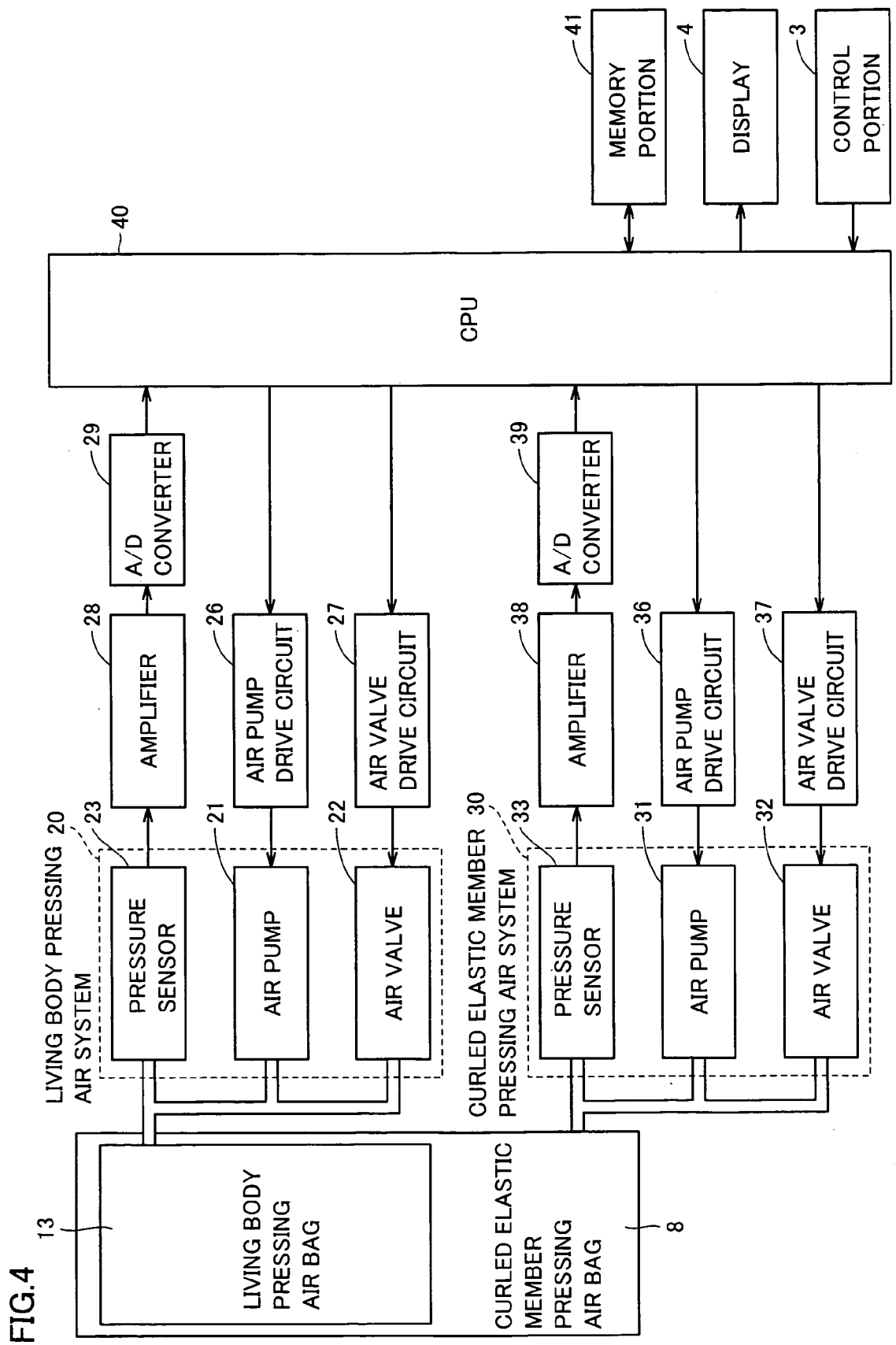
FIG. 4 is a functional block diagram of the blood pressure monitor shown in FIG. 1.

As shown in FIG. 4, the above-described living body pressing air bag 13 and curled elastic member pressing air bag 8 are connected to living body pressing air system 20 and curled elastic member pressing air system 30, respectively. Further, living body pressing air system 20 and curled elastic member pressing air system 30 have their operations controlled by a CPU (central processing unit) 40.

Living body pressing air system 20 includes an air pump 21, an air valve 22, and a pressure sensor 23. Air pump 21 is means for pressurizing bladder 13c of living body pressing air bag 13, which is driven by an air pump drive circuit 26 having received a command from CPU 40. Upon measurement, air pump 21 introduces compressed gas into bladder 13c of living body pressing air bag 13 to make bladder 13c attain a prescribed pressure. Air valve 22 is means for keeping or reducing the pressure in bladder 13c of living body pressing air bag 13, which is controlled to open and close by an air valve drive circuit 27 having received a command from CPU 40. Upon measurement, air valve 22 functions to keep and reduce the pressure of bladder 13c of living body pressing air bag 13 having attained a high-pressure state by air pump 21. After completion of the measurement, air valve 22 causes bladder 13c of living body pressing air bag 13 to return to the atmospheric pressure. Pressure sensor 23 is means for detecting a pressure of bladder 13c of living body pressing air bag 13. Upon measurement, pressure sensor 23 detects the pressure of bladder 13c of living body pressing air bag 13 that changes from moment to moment, and outputs signals corresponding to the detected values to an amplifier 28. Amplifier 28 amplifies the signals output from pressure sensor 23 and outputs the amplified signals to an A/D converter 29. A/D converter 29 digitalizes the analog signals received from amplifier 28, and outputs the resultant signals to CPU 40.

Curled elastic member pressing air system 30 includes an air pump 31, an air valve 32, and a pressure sensor 33. Air pump 31 is means for pressurizing bladder 8c of curled elastic member pressing air bag 8, which is driven by an air pump drive circuit 36 having received a command from CPU 40, and introduces compressed gas into bladder 8c of curled elastic member pressing air bag 8 at the start of measurement such that bladder 8c attains a prescribed pressure. Air valve 32 is means for keeping and reducing the pressure of bladder 8c of curled elastic member pressing air bag 8, which is controlled to open and close by an air valve drive circuit 37 having received a command from CPU 40. Upon measurement, air valve 32 keeps the pressure of bladder 8c of curled elastic member pressing air bag 8 having attained a high-pressure state by air pump 31, and after completion of the measurement, it causes bladder 8c to return to the atmospheric pressure. Pressure sensor 33 is means for detecting the pressure of bladder 8c of curled elastic member pressing air bag 8. At the start of measurement, pressure sensor 33 detects the pressure of bladder 8c of curled elastic member pressing air bag 8 and outputs a signal corresponding to the detected value to an amplifier 38. Amplifier 38 amplifies the signal output from pressure sensor 33, and outputs the amplified signal to an A/D converter 39. A/D converter 39 digitalizes the analog signal received from amplifier 38, and outputs the resultant signal to CPU 40.

CPU 40 controls living body pressing air system 20 and curled elastic member pressing air system 30 based on commands input via control portion 3 provided at base unit 2 of blood pressure monitor 1, and outputs a result of measurement to display portion 4 and a memory portion 41. Memory portion 41 is means for storing the measurement results.

Blood pressure monitor 1 of the present embodiment starts a measurement operation when a subject or the like depresses the measurement button provided at control portion 3 of base unit 2. Hereinafter, the measurement operation in blood pressure monitor 1 will be described step by step.

Figure 5:
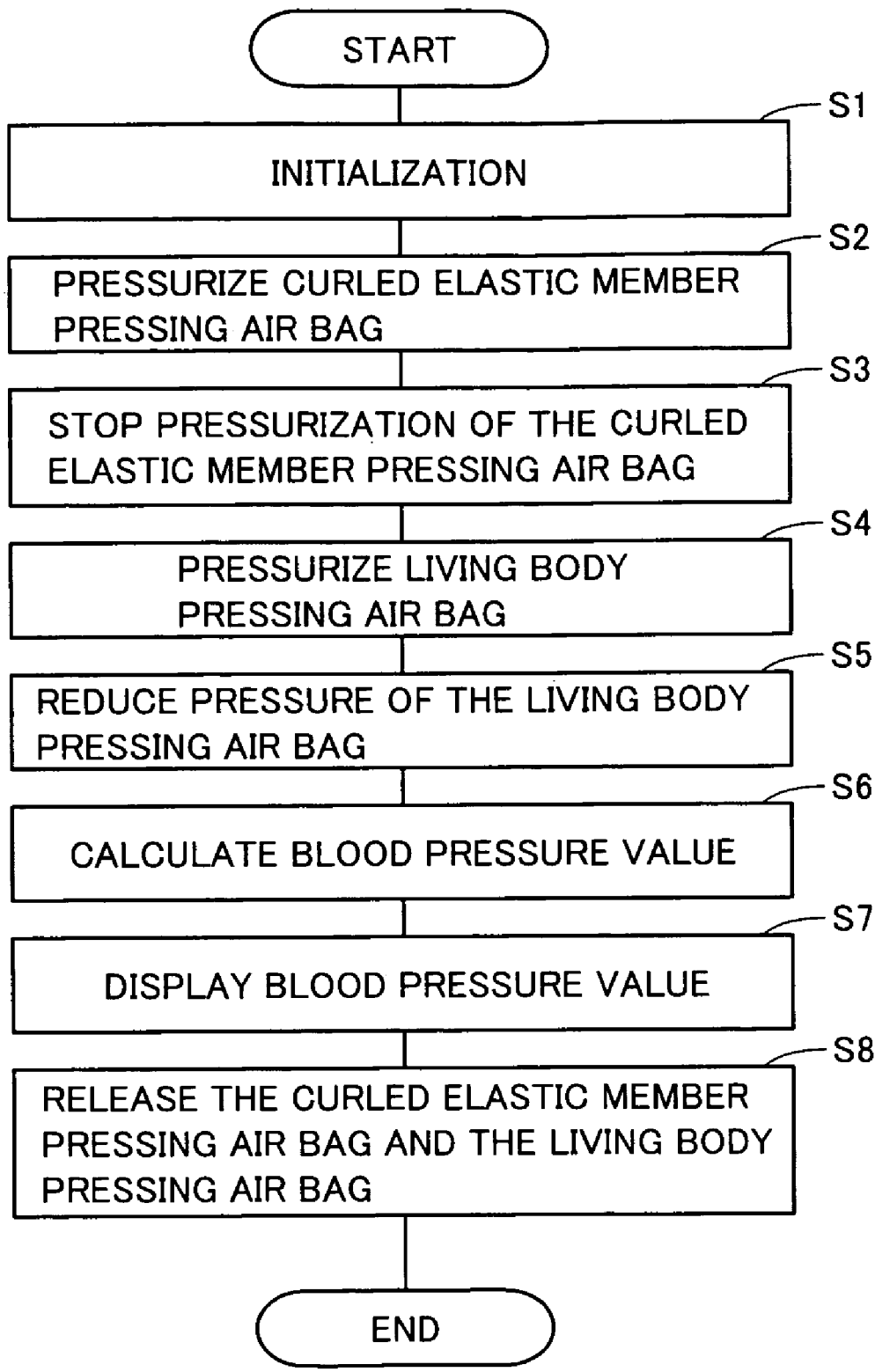
FIG. 5 is a flowchart illustrating a measurement operation of the blood pressure monitor shown in FIG. 1.

As shown in FIG. 5, firstly, in step 1, blood pressure monitor 1 is initialized. Next, in step 2, curled elastic member pressing air bag 8 is pressurized. The pressurization is stopped when the pressure of bladder 8c of curled elastic member pressing air bag 8 attains a prescribed pressure (step 3). Next, in step 4, living body pressing air bag 13 is pressurized, which is stopped when the pressure of bladder 13c of living body pressing air bag 13 attains a prescribed pressure. In step 5, arterial pressure pulse waves are detected while the pressure of living body pressing air bag 13 is being reduced. Thereafter, in step 6, a blood pressure value is calculated based on the detected data of the arterial pressure pulse waves. In step 7, the blood pressure value is displayed on display portion 4 provided at base unit 2, while in step 8, bladder 8c of curled elastic member pressing air bag 8 and bladder 13c of living body pressing air bag 13 are released to the atmospheric pressure.

Figure 6:
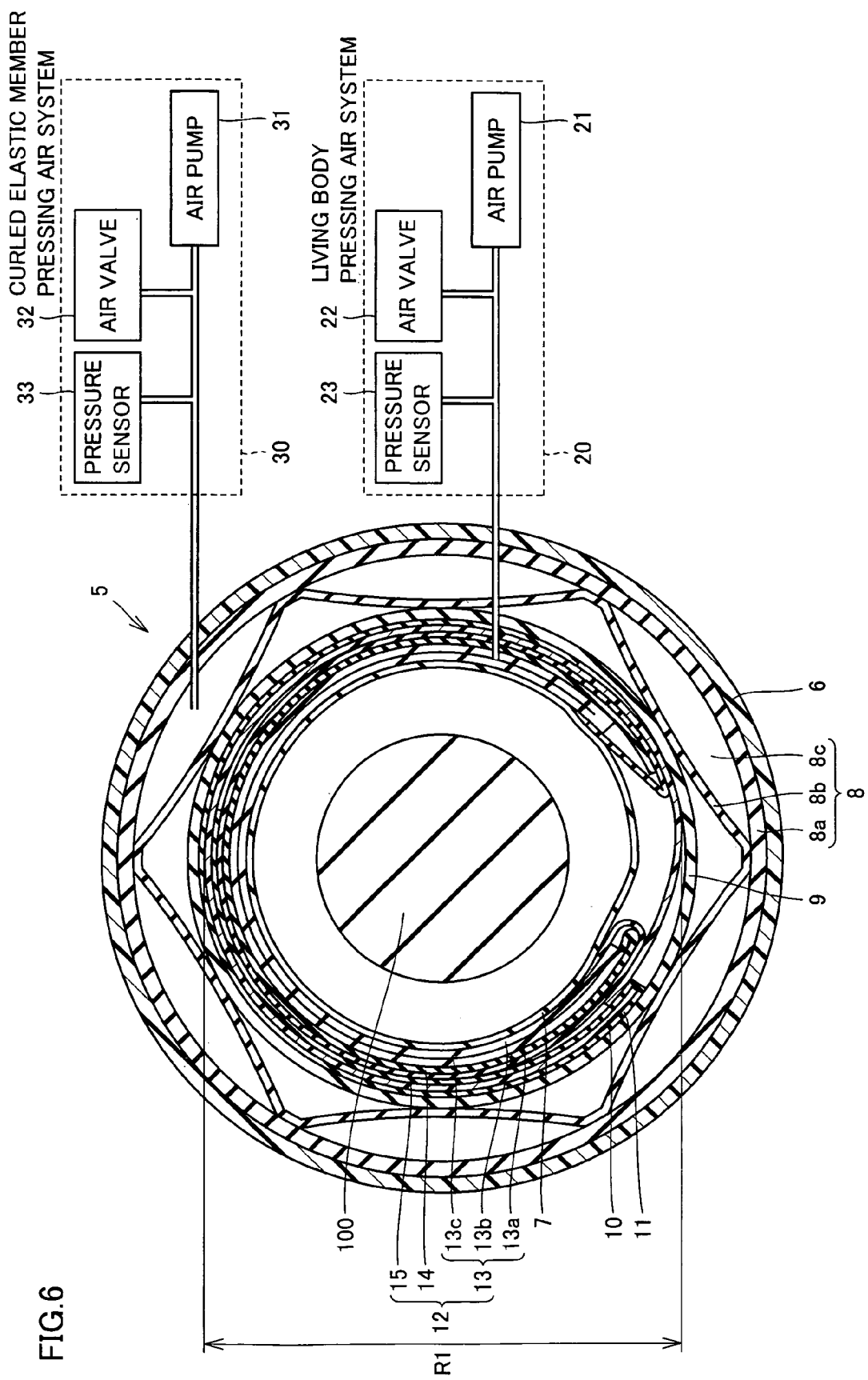
FIG. 6 schematically illustrates inflating/deflating operations of a curled elastic member pressing air bag and a living body pressing air bag, showing the state before start of the measurement operation.

As shown in FIG. 6, in the non-pressurized state where curled elastic member pressing air bag 8 and living body pressing air bag 13 are released to the atmospheric pressure, curled elastic member pressing air bag 8 and living body pressing air bag 13 are both in a deflated state. Thus, there is substantially no external force acting on curled elastic member 10 located between curled elastic member pressing air bag 8 and living body pressing air bag 13. This means that measuring portion 5 has a sufficient inner space to let upper arm 100 inserted therein, which is adaptable to a wide range from children, elderly people and adult women having upper arms of relatively small cross sections, to adult men having upper arms of relatively large cross sections. It is noted that in the non-pressurized state shown in FIG. 6, living body pressing air bag 13 has its ends in the circumferential direction spaced apart from each other.

Figure 7:
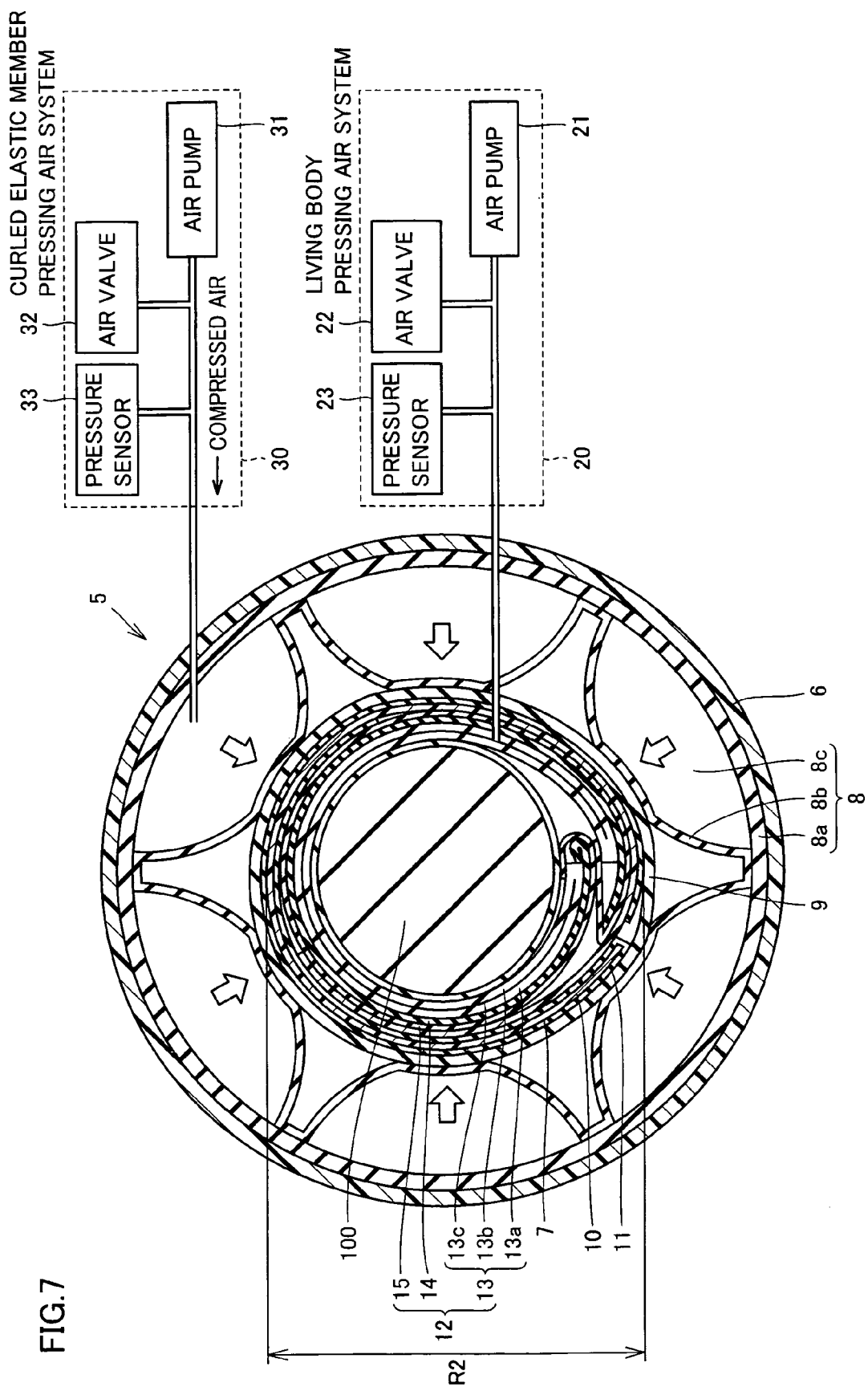
FIG. 7 schematically illustrates the inflating/deflating operations of the curled elastic member pressing air bag and the living body pressing air bag, showing the state where a curled elastic member pressing air system is activated to inflate the curled elastic member pressing air bag.

As shown in FIG. 7, in the first pressurized state where curled elastic member pressing air bag 8 is pressurized by curled elastic member pressing air system 30, curled elastic member pressing air bag 8 has its outer peripheral layer 8a bound by shell 6, preventing its outward inflation in the radial direction, so that it is inflated only inward in the radial direction. With this inflation of curled elastic member pressing air bag 8, the outer peripheral surface of curled elastic member 10 is pressed inward by inner peripheral layer 8b of curled elastic member pressing air bag 8, and thus, the ends of curled elastic member 10 move toward the direction to reduce the diameter of curled elastic member 10. Specifically, one end in the circumferential direction of curled elastic member 10 subducts more deeply under the other end, leading to reduction in size of curled elastic member 10 in the radial direction. Thus, a diameter R2 of curled elastic member 10 in the first pressurized state is smaller than a diameter R1 of curled elastic member 10 in the above-described non-pressurized state shown in FIG. 6.

With reduction in diameter of curled elastic member 10, living body pressing air bag 13 disposed on the inside of curled elastic member 10 is also reduced in diameter. As such, living body pressing air bag 13 is pressed against the surface of upper arm 100. In the state shown in FIG. 7, the ends of living body pressing air bag 13 in the circumferential direction partly overlap with each other.

Figure 8:
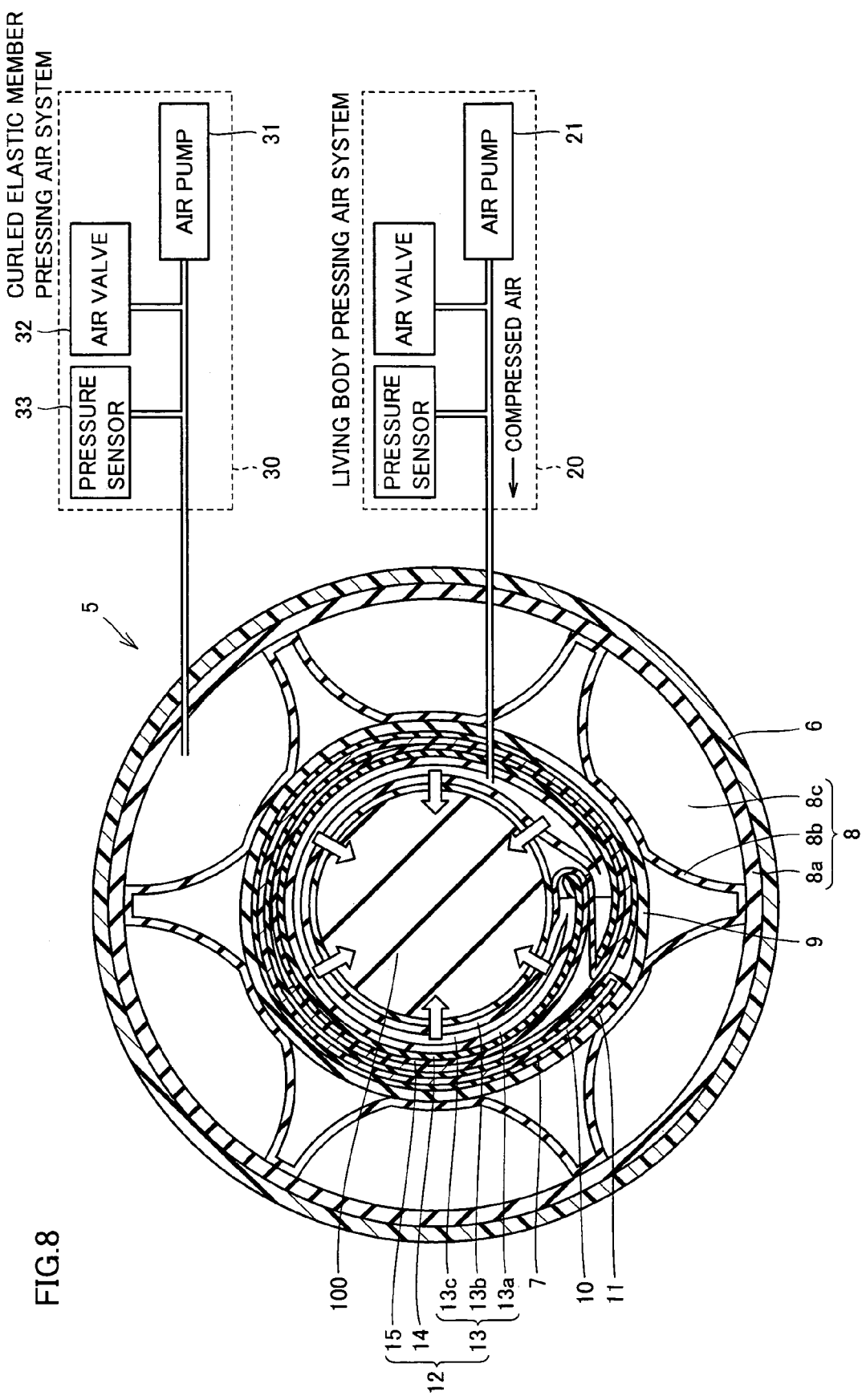
FIG. 8 schematically illustrates the inflating/deflating operations of the curled elastic member pressing air bag and the living body pressing air bag, showing the state where a living body pressing air system is activated to inflate the living body pressing air bag.

As shown in FIG. 8, in the second pressurized state where living body pressing air bag 13 is pressurized by living body pressing air system 20, living body pressing air bag 13 has its outer peripheral layer 13a bound by curled elastic member pressing air bag 8. As such, inflation of living body pressing air bag 13 outward in the radial direction is substantially suppressed, and it is inflated only inward in the radial direction. With the inflation of living body pressing air bag 13, upper arm 100 is pressed and secured, and the artery located within upper arm 100 is pressed. A blood pressure value is measured as living body pressing air bag 13 is gradually reduced in pressure from the second pressurized state.

In the inflating/deflating operations illustrated in FIGS. 6–8, there occurs large friction at the contact surface of living body pressing air bag 13 and curled elastic member 10 as well as at the contact surface of curled elastic member 10 and curled elastic member pressing air bag 8. Thus, in the living body pressing and securing device of the present embodiment, cloth 15 and cloth bag 11 serving as the low-friction members are arranged between living body pressing air bag 13 and curled elastic member 10, and cloth 9 and cloth bag 11 serving as the low-friction members are also arranged between curled elastic member 10 and curled elastic member pressing air bag 8, to realize smooth sliding. The friction would otherwise be superimposed on the detected value of the pressure sensor in the form of a noise. The configuration of the present embodiment suppressing such friction can improve accuracy in measurement of the blood pressure value.

In the living body pressing and securing device of the present embodiment described above, the curled elastic member pressing air bag has been employed as means for winding the curled elastic member around a living body. When the curled elastic member pressing air bag is arranged all around the outside of the curled elastic member, the outer peripheral surface of the curled elastic member can be pressed uniformly over the entire surface, so that it is possible to wind the curled elastic member around the living body without causing twisting of the living body. As a result, skin tension will hardly occur on the surface of the living body, and uniform winding strength is realized over the entire surface of the site being pressed, thereby enabling accurate and stable measurement of the blood pressure value.

Further, in the living body pressing and securing device of the present embodiment, the curled elastic member winding mechanism is configured with the curled elastic member pressing air bag. Thus, the parts required for the winding mechanism are only the air pump, the air valve, an air tube for connecting them with the curled elastic member pressing air bag, and the pressure sensor for detecting the pressure within the curled elastic member pressing air bag. Accordingly, it is possible to realize a winding mechanism simplified and downsized compared to the one of a conventional living body pressing and securing device employing an electric motor.

Figure 9:
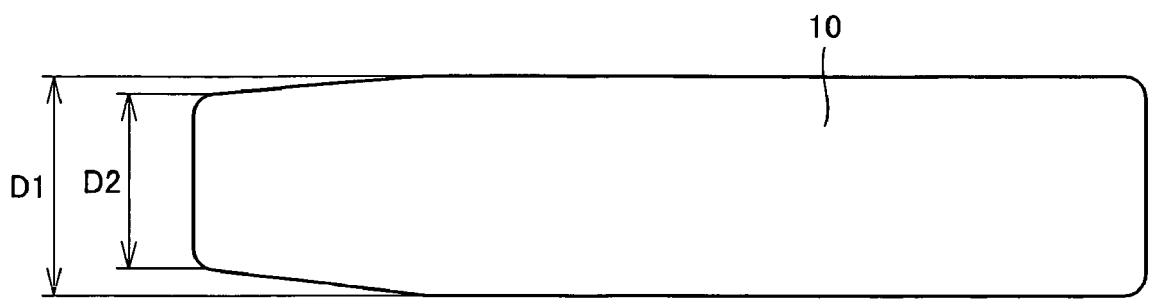
FIG. 9 is an exploded diagram of the curled elastic member of the living body pressing and securing device according to the embodiment of the present invention.

As shown in FIG. 9, curled elastic member 10 of the living body pressing and securing device of the present embodiment is configured to have a length D1 in the axial direction in the vicinity of one end in the circumferential direction that is shorter than a length D2 in the axial direction in the vicinity of the center in the circumferential direction. That is, in the exploded state of curled elastic member 10, curled elastic member 10 is tapered on one of the edge portions extending in the longitudinal direction.

Figure 10:
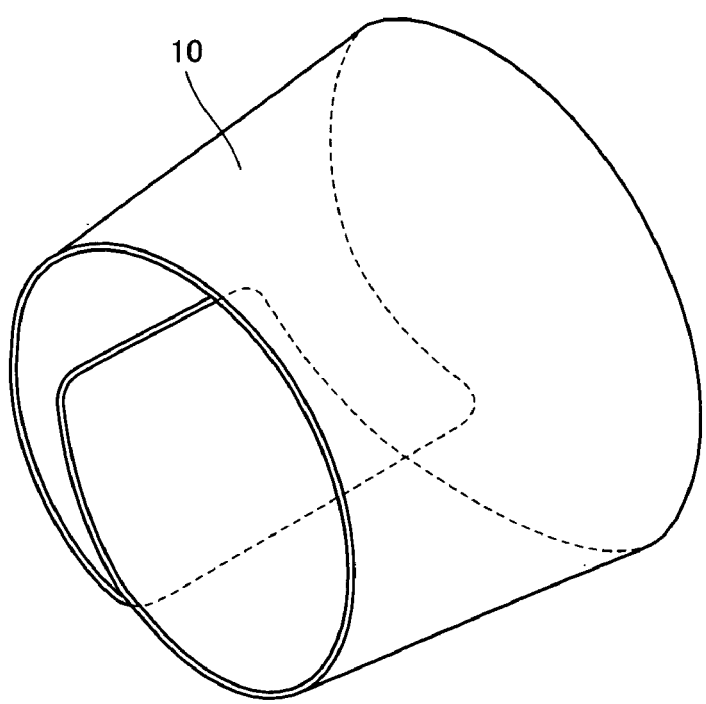
FIG. 10 is a perspective view of the curled elastic member of FIG. 9, showing its shape when reduced in diameter.

As shown in FIG. 10, when curled elastic member 10 having such a shape is reduced in diameter, even in the case where pressing force varies in the axial direction over the outer peripheral surface of curled elastic member 10 (i.e., even if the upper arm to which the curled elastic member is to be pressed increases or decreases in thickness at an end corresponding to the distal end of the living body), it is ensured that the tapered end in the circumferential direction of curled elastic member 10 comes to overlap with the other end not tapered, thereby preventing the corners of curled elastic member 10 from protruding outward.

Figure 11:
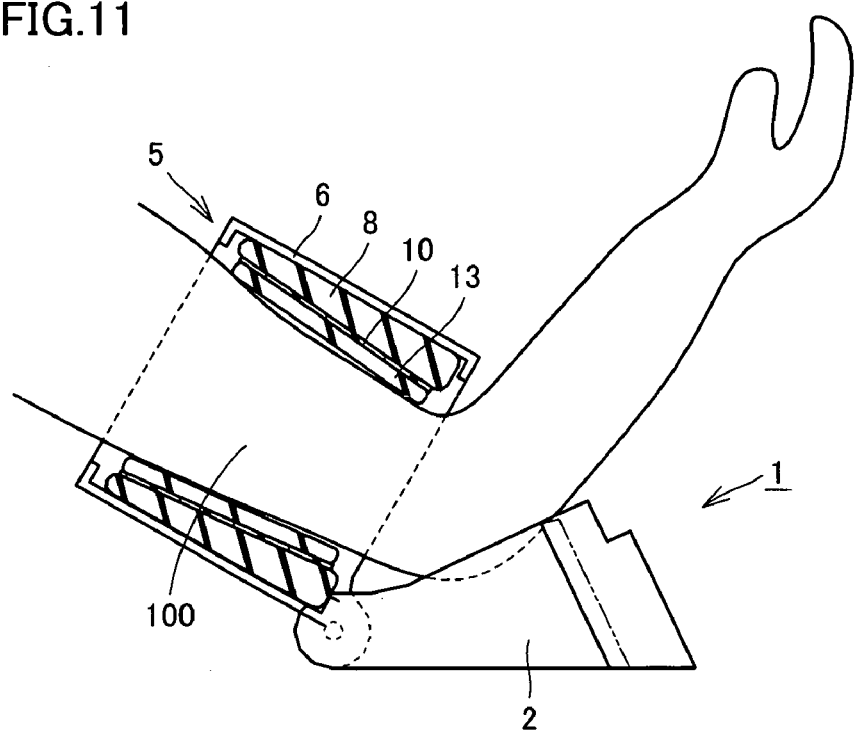
FIG. 11 is a schematic cross sectional view showing the state where the living body pressing and securing device of the present embodiment is employed to press and secure the upper arm that has an outer shape tapered toward its distal end.

In the living body pressing and securing device of the present embodiment, curled elastic member 10 having the shape as shown in FIGS. 9 and 10 is employed. Thus, as shown in FIG. 11, curled elastic member 10 can fit to upper arm 100, even if it has an outer shape tapered toward the distal end, as curled elastic member 10 is bent as appropriate. Specifically, at the tapered distal end of the upper arm, curled elastic member 10 is further reduced in diameter, so that it can fit to upper arm 100 having its outer shape tapered toward the distal end. As such, using the curled elastic member having the shape as shown in FIGS. 9 and 10 enables the curled elastic member to be fitted to an upper arm irrelevant to its outer shape, and fastening strength of the curled elastic member can be kept uniform over its axial direction.

Further, when using the curled elastic member having the shape as shown in FIGS. 9 and 10, the corner portions of curled elastic member 10 would not protrude outward upon reduction in diameter, which would otherwise press upper arm 100 of a subject in the vicinity of the site subjected to measurement. This prevents the subject from feeling uncomfortable. Furthermore, with the corner portions of curled elastic member 10 being bound by the surrounding member, deformation of curled elastic member 10 is prevented, ensuring sufficient securing of upper arm 100 by pressing.

A living body pressing and securing device needs to be adaptable to a wide variety of users from children, elderly people and adult women having upper arms of relatively small cross sections to adult men having upper arms of relatively large cross sections, as already described above. Thus, it is necessary for the ends in the circumferential direction of living body pressing air bag 13, which are spaced apart from each other in the non-pressurized state, to smoothly overlap with each other when the diameter is being reduced. However, since living body pressing air bag 13 is formed of a material having relatively small rigidity, it would be very difficult for the ends to smoothly overlap with each other unless a certain measure is conducted.

Figure 12:
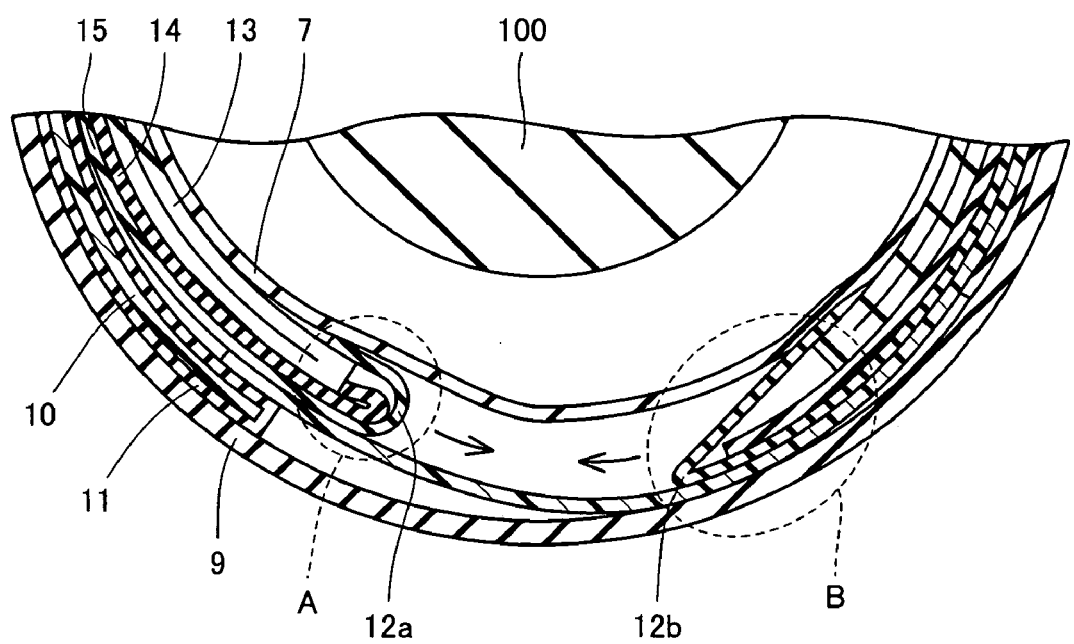
FIG. 12 is an enlarged cross sectional view of the end portions in the circumferential direction of the living body pressing air bag, at the time of the inflating/deflating operations shown in FIG. 6.

In view of the foregoing, in the living body pressing and securing device of the present embodiment, for the purpose of realizing such smooth overlapping of the ends in the circumferential direction of living body pressing air bag 13, one end A in the circumferential direction of living body pressing unit 12 is provided with a curved portion 12a at its tip end, and the other end B is provided with a sharp portion 12b at its tip end, as shown in FIG. 12. Specifically, one end in the circumferential direction of resin plate 14 is bent to have a certain radius of curvature, and cloth 15 is adhered to resin plate 14 to cover the bent portion thereof, to thereby form curved portion 12a. As to the other end in the circumferential direction of resin plate 14, cloth 15 folded in an acute angle is adhered to cover the same, to form sharp portion 12b.

Figure 13:
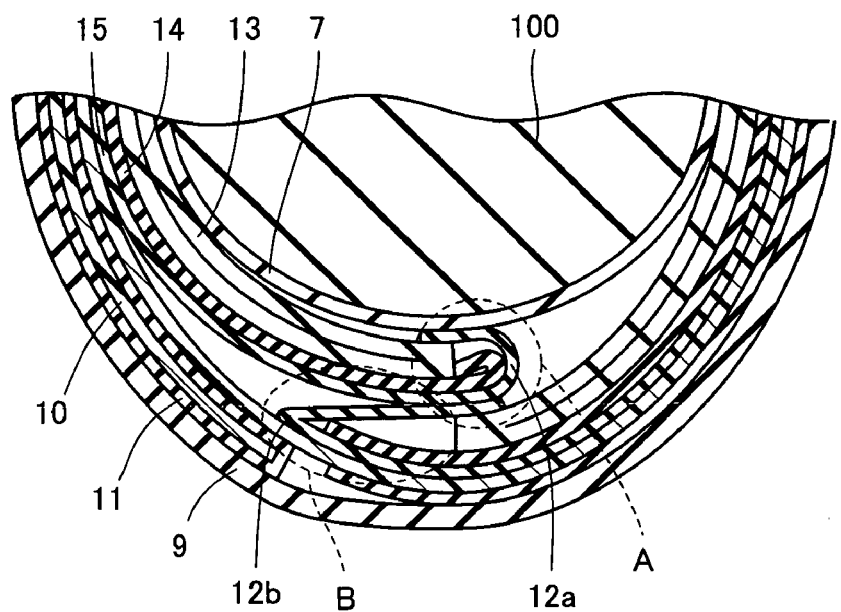
FIG. 13 is an enlarged cross sectional view of the end portions in the circumferential direction of the living body pressing air bag, at the time of the inflating/deflating operations shown in FIG. 7.

With this configuration, upon reduction in diameter of curled elastic member 10, curved portion 12a smoothly runs on sharp portion 12b, as shown in FIG. 13. This prevents the ends of living body pressing air bag 13 from colliding with each other, which would otherwise cause one end to be bent or curled up to hinder reduction in diameter of living body pressing air bag 13. Accordingly, the friction caused at the overlapping portion of living body pressing air bag 13 at the time of reduction or increase in diameter thereof is reduced, and thus, superimposition of the friction to the detected value of the pressure sensor in the form of a noise is prevented. As a result, accuracy in measurement of the blood pressure value is improved. It is noted that various configurations other than the one described above can be employed to form the curved portion and the sharp portion at the ends in the circumferential direction of the living body pressing unit, and the device configuration and specification of the living body pressing and securing device can also be modified as appropriate.

Figure 14:
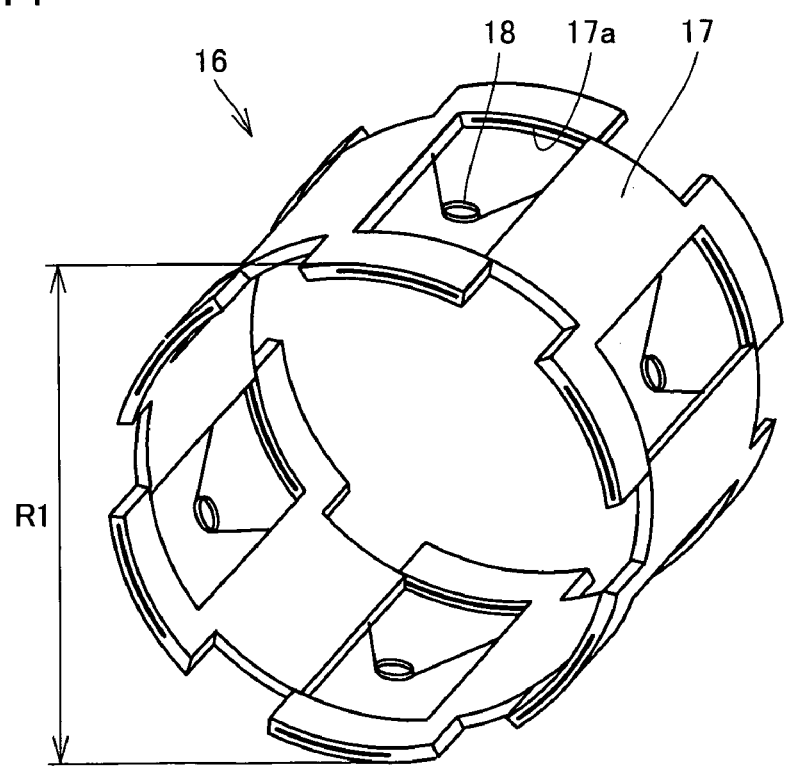
FIG. 14 is a perspective view of a modification in configuration of the curled elastic member of the living body pressing and securing device according to the embodiment of the present invention, showing the shape of the curled elastic member in the non-pressurized state.

In the living body pressing and securing device according to the present invention, a curled elastic member 16 having a configuration as shown in FIG. 14 may be employed as well. Curled elastic member 16 shown in FIG. 14 is formed of a plurality of segments 17 and a plurality of elastic connectors 18 that are alternately arranged in the circumferential direction. Segment 17 is formed of a resin member having a cross section in the circumferential direction shaped in an arc, as shown, for example, in FIG. 14. The segment is slidably connected with the neighboring segment by means of a rail 17a and a projection (not shown) that engages with rail 17a. Elastic connector 18 is formed of a coil spring, as shown, for example, in FIG. 14, which connects the neighboring segments 17 with each other and, at the same time, elastically biases them to keep them away from each other.

Figure 15:
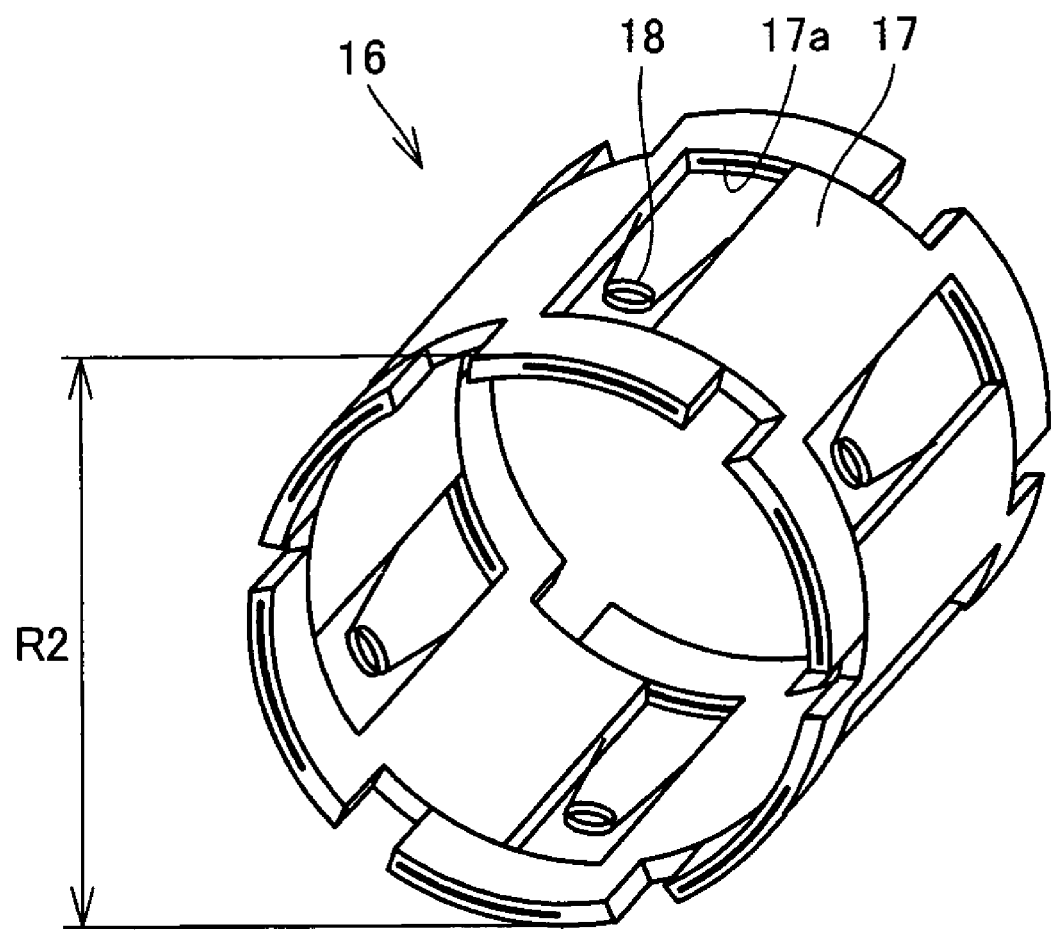
FIG. 15 is a perspective view of the modification in configuration of the curled elastic member of the living body pressing and securing device according to the embodiment of the present invention, showing the shape of the curled elastic member when reduced in diameter.
Figure 16:
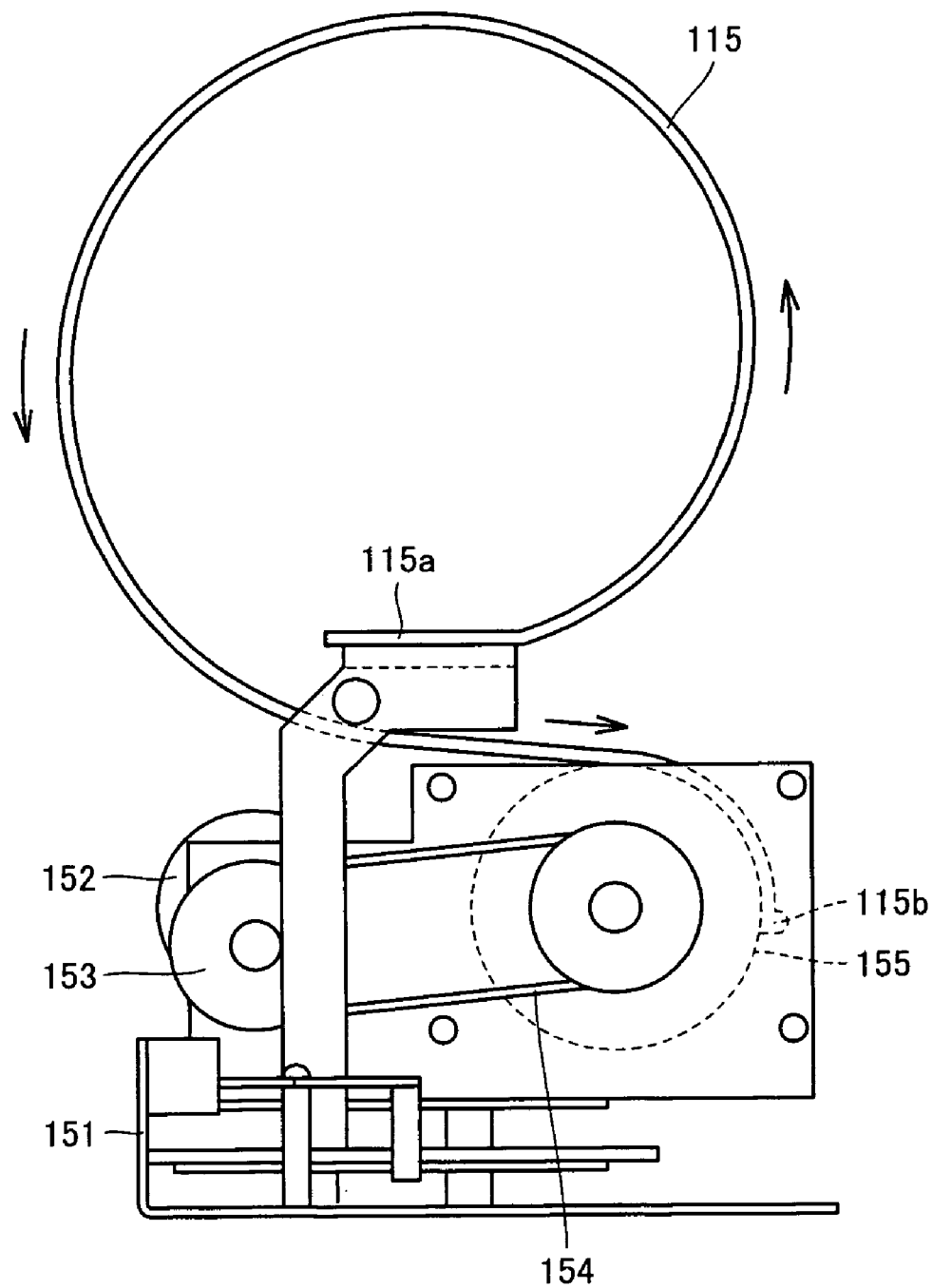
FIG. 16 is a front view showing by way of example a configuration of a conventional automatic cuff winding device.

Provided on the outside of curled elastic member 16 is a curled elastic member pressing air bag, as in the living body pressing and securing device described above. A living body pressing air bag is also disposed inside curled elastic member 16, again as in the above-described living body pressing and securing device. With this configuration, curled elastic member 16 has its outer peripheral surface pressed inward as the curled elastic member pressing air bag is inflated, so that curled elastic member 16 is reduced in diameter as shown in FIG. 15, in opposition to the elastic bias force of elastic connectors 18. When the curled elastic member pressing air bag is deflated and the pressure against curled elastic member 16 is released, segments 17 move to keep away from each other by the elastic bias force of elastic connectors 18, and thus, curled elastic member 16 recovers the shape as shown in FIG. 14.

Using the curled elastic member having the configuration as described above can also realize a curled elastic member changeable in size in the radial direction, as in the case of using the above-described curled elastic member formed of the plate member wound into an approximately cylindrical shape. Accordingly, the living body pressing and securing device employing such a curled elastic member can also enjoy the effects similar to those as described above.

In the embodiment described above, an air bag having compressed air introduced therein has been employed for each of the living body pressing fluid bag and the elastic member pressing fluid bag. However, they are not restricted to the air bags. It is of course possible to configure the living body pressing fluid bag and the elastic member pressing fluid bag with gas bags having other gas introduced therein or liquid bags having liquid introduced therein.

Further, in the above-described embodiment, the application of the living body pressing and securing device of the present invention to a blood pressure monitor for use in measurement of a blood pressure value by securing the upper arm by pressing has been explained by way of example. However, the present invention is naturally applicable to a wrist blood pressure monitor as well. Still further, not limited to the blood pressure motor, it is applicable to a pulse wave detecting device and others. Furthermore, the use of the living body pressing and securing device of the present invention is not limited to pressing and securing of the upper arm. It is applicable to pressing and securing of any site of a living body including forearm, lower limb, torso and others.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A blood pressure monitor, comprising:
    a living body pressing fluid bag for pressing a living body;
    a separate elastic member of an approximately cylindrical shape, disposed on the outside of said living body pressing fluid bag and changeable in size in a radial direction;
    an elastic member pressing fluid bag, disposed on the outside of said elastic member and inflated to press an outer peripheral surface of said elastic member inward to reduce a diameter of said elastic member, to thereby press said living body pressing fluid bag against the living body via said elastic member;
    a frame disposed on the outside of the elastic member pressing fluid bag to restrict inflation of the elastic member pressing bag in a radially outward direction;
    a pressure sensing unit for sensing a pressure inside said living body pressing fluid bag; and
    a blood pressure value calculating unit for calculating a blood pressure value based on information sensed by said pressure sensing unit.

2. The blood pressure monitor according to claim 1, wherein said elastic member is formed of segments and elastic connectors alternately arranged in a circumferential direction, and each of said elastic connectors connects neighboring ones of said segments and, at the same time, elastically biases the neighboring segments to keep them away from each other.

3. The blood pressure monitor according to claim 1, wherein said elastic member is formed of a plate member wound into an approximately cylindrical shape and having a discontinuous portion that extends in an axial direction and is disposed at a position in a circumferential direction.

4. The blood pressure monitor according to claim 3, wherein a portion of said plate member in the vicinity of at least one end in a circumferential direction has a length in an axial direction of said plate member that is shorter than a length in the axial direction of said plate member in the vicinity of the center of said plate member in the circumferential direction.

5. The blood pressure monitor according to claim 1, wherein an end of said living body pressing fluid bag in a circumferential direction has a tip end provided with a curved portion, and the other end of said living body pressing fluid bag in the circumferential direction has a tip end provided with a sharp portion, and said curved portion runs on said sharp portion when said elastic member is reduced in diameter.

6. The blood pressure monitor according to claim 1, wherein a low-friction member is arranged between said elastic member and said living body pressing fluid bag to reduce friction therebetween.

7. The blood pressure monitor according to claim 6, wherein said low-friction member is a piece of cloth.

8. The blood pressure monitor according to claim 1, wherein a low-friction member is arranged between said elastic member and said elastic member pressing fluid bag to reduce friction therebetween.

9. The blood pressure monitor according to claim 8, wherein said low-friction member is a piece of cloth.

* * * * *